US011090480B2

(12) United States Patent  (10) Patent No.: US 11,090,480 B2
Ciccone et al.  (45) Date of Patent: Aug. 17, 2021

(54) CONNECTOR SYSTEM

(71) Applicant: WilMarc Holdings, LLC, Fort Collins, CO (US)

(72) Inventors: Paul C. Ciccone, Wellington, CO (US); William A. Coulson, Fort Collins, CO (US); Marcia Coulson, Fort Collins, CO (US)

(73) Assignee: Wilmarc Holdings, LLC, Fort Collins, CO (US)

( * ) Notice: Subject to any disclaimer, the term of this patent is extended or adjusted under 35 U.S.C. 154(b) by 0 days.

(21) Appl. No.: 16/888,263

(22) Filed: May 29, 2020

(65) Prior Publication Data
US 2020/0289812 A1 Sep. 17, 2020

Related U.S. Application Data

(63) Continuation of application No. 15/878,240, filed on Jan. 23, 2018, now Pat. No. 10,668,269, which is a (Continued)

(51) Int. Cl.
*F16L 39/00* (2006.01)
*A61M 39/24* (2006.01)
(Continued)

(52) U.S. Cl.
CPC ............ *A61M 39/24* (2013.01); *A61M 39/10* (2013.01); *F16L 29/00* (2013.01); *F16L 39/00* (2013.01);
(Continued)

(58) Field of Classification Search
CPC ........ A61M 39/24; A61M 39/10; F16L 29/00; F16L 39/00
See application file for complete search history.

(56) References Cited

U.S. PATENT DOCUMENTS 6,345,936 B2 * 2/2002 Pfeiffer .................. B65G 53/14
  406/197
6,371,161 B1 4/2002 Hua
  (Continued)

FOREIGN PATENT DOCUMENTS

CA  1021656  11/1977
DE  102004015703  11/2005
  (Continued)

OTHER PUBLICATIONS

U.S. Appl. No. 62/063,896, filed Oct. 14, 2014.
(Continued)

*Primary Examiner* — Kevin L Lee
(74) *Attorney, Agent, or Firm* — Craig R. Miles; CR Miles P.C.

(57) ABSTRACT

A connector which couples to an outlet conduit to decrease an outlet conduit passageway pressure differential between outlet conduit opposing first and second ends, whereby the connector includes a mixing chamber having a first inlet port in fluidic communication with a connector first open end and the mixing chamber; an outlet port in fluidic communication with the mixing chamber and a connector second open end; and a second inlet port in fluidic communication with the connector second open end and the mixing chamber. Additionally, a connector including a connector internal surface defining a connector passageway which communicates between connector first and second open ends; and a sensor module operatively coupled to the connector passageway to sense a parameter of a first fluid flowing in a first fluid flow path through the connector passageway.

16 Claims, 11 Drawing Sheets

Related U.S. Application Data continuation of application No. 14/883,531, filed on Oct. 14, 2015, now Pat. No. 9,878,144.

(60) Provisional application No. 62/063,896, filed on Oct. 14, 2014.

(51) Int. Cl.
*F16L 29/00* (2006.01)
*F16L 55/07* (2006.01)
*A61M 39/10* (2006.01)

(52) U.S. Cl.
CPC .......... *F16L 55/07* (2013.01); *A61M 2205/33* (2013.01); *A61M 2205/3324* (2013.01); *A61M 2205/3331* (2013.01)

(56) References Cited

U.S. PATENT DOCUMENTS

| | | | |
|---|---|---|---|
| 6,858,381 | B2 | 2/2005 | Ichikawa et al. |
| 7,815,700 | B2 | 10/2010 | Bartolini et al. |
| 8,101,417 | B2 | 1/2012 | Conway et al. |
| 9,878,144 | B2 | 1/2018 | Ciccone et al. |
| 10,668,269 | B2 | 6/2020 | Ciccone et al. |
| 2012/0001731 | A1 | 1/2012 | Potyrailo et al. |
| 2013/0068316 | A1 | 3/2013 | Gueneron |
| 2014/0276740 | A1* | 9/2014 | Larson et al. ......... A61B 18/00 606/33 |

FOREIGN PATENT DOCUMENTS

| | | |
|---|---|---|
| FR | 2960425 | 12/2011 |
| WO | 01/10362 | 2/2001 |
| WO | 2012/125024 | 9/2012 |
| WO | 2015/095363 | 6/2015 |

OTHER PUBLICATIONS

Parallel European Patent Application No. 16000568.2; Office Action with Partial European Search Report dated Sep. 26, 2016, 6 pages total.

Parallel European Patent Application No. 16000568.2; Office Action with European Search Report dated Nov. 21, 2016, 12 pages total.

* cited by examiner

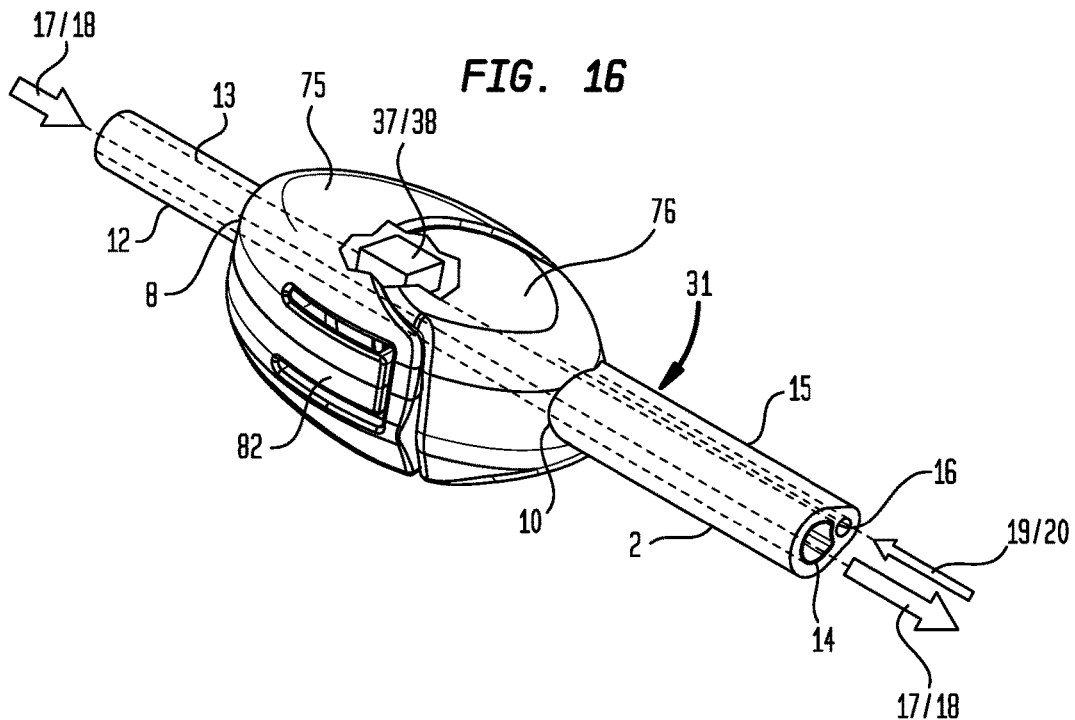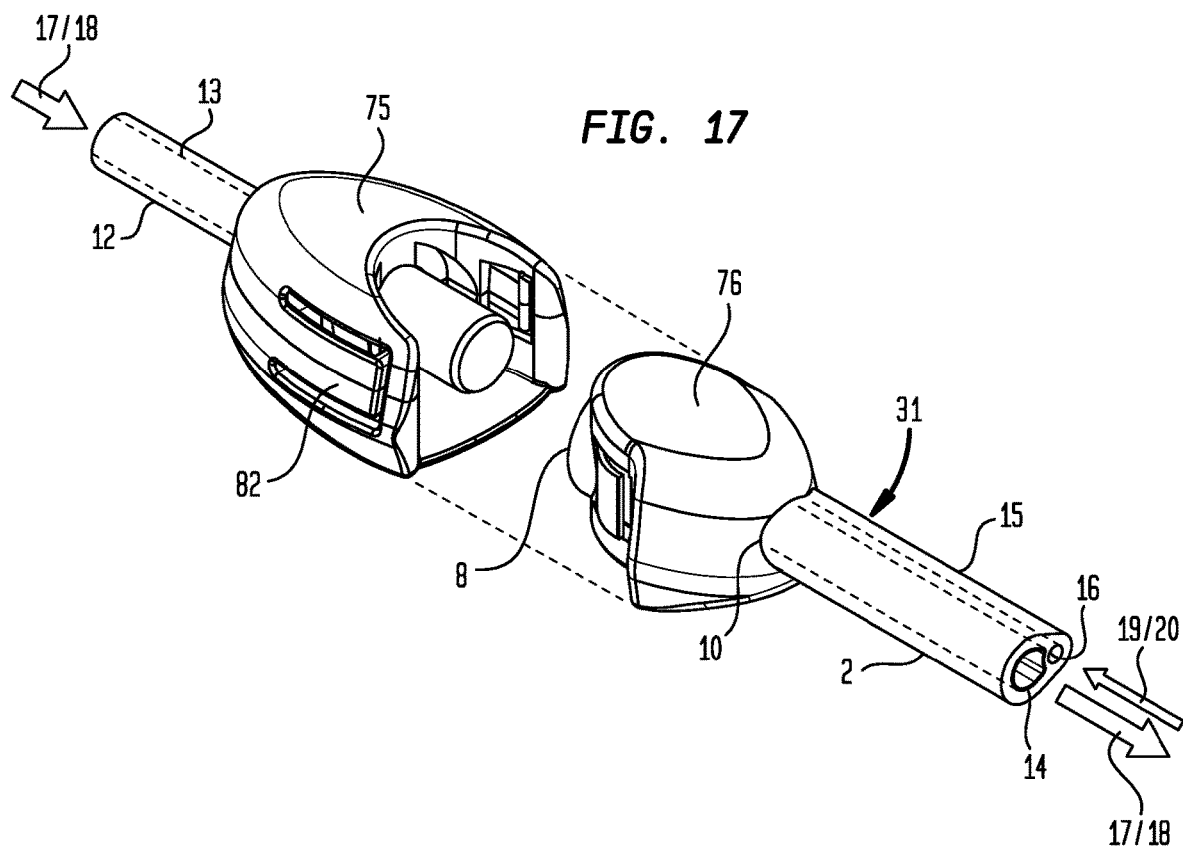

CONNECTOR SYSTEM

This United States Patent Application is a continuation of U.S. patent application Ser. No. 15/878,240, filed Jan. 23, 2018, now U.S. Pat. No. 10,668,269, issued Jun. 2, 2020, which is a continuation of U.S. patent application Ser. No. 14/883,531, filed Oct. 14, 2015, now U.S. Pat. No. 9,878,144, issued Jan. 30, 2018, which claims the benefit of U.S. Provisional Patent Application No. 62/063,896, filed Oct. 14, 2014, each hereby incorporated by reference herein.

I. SUMMARY OF THE INVENTION

A broad object of a particular embodiment of the invention can be to provide a connector which couples to an outlet conduit to decrease an outlet conduit passageway pressure differential between outlet conduit opposing first and second ends, and methods of making and using such a connector, whereby the connector includes a mixing chamber having a first inlet port in fluidic communication with a connector first open end and the mixing chamber; an outlet port in fluidic communication with the mixing chamber and a connector second open end; and a second inlet port in fluidic communication with the connector second open end and the mixing chamber.

Another broad object of a particular embodiment of the invention can be to provide a connector whereby the connector first open end is configured to couple to a first inlet conduit to fluidicly couple a first inlet conduit passageway to the first inlet port; whereby the connector second open end is configured to couple to an outlet conduit to fluidicly couple an outlet conduit passageway to the outlet port; and whereby the connector second open end is further configured to couple to a second inlet conduit to fluidicly couple a second inlet conduit passageway to the second inlet port.

Another broad object of a particular embodiment of the invention can be to provide a connector whereby the first inlet conduit passageway, the first inlet port, the mixing chamber, the outlet port, and the outlet conduit passageway define a first fluid flow path in which a first fluid flows; whereby the second inlet conduit passageway, the second inlet port, and the mixing chamber define a second fluid flow path in which a second fluid flows; and whereby the second fluid mixes with the first fluid in the mixing chamber to decrease the outlet conduit passageway pressure differential.

Another broad object of a particular embodiment of the invention can be to provide a connector, and methods of making and using such a connector, whereby the connector includes a connector internal surface defining a connector passageway which communicates between connector first and second open ends; and a sensor module operatively coupled to the connector passageway to sense a parameter of a first fluid flowing in a first fluid flow path through the connector passageway.

Naturally, further objects of the invention are disclosed throughout other areas of the specification, drawings, and claims.

II. A BRIEF DESCRIPTION OF THE DRAWINGS

FIG. 16 is a perspective view of a particular embodiment of a connector comprising first and second housings, whereby an inlet conduit is coupled to a connector first open end defined by the first housing, and an outlet conduit and a second inlet conduit are coupled to a connector second open end defined by the second housing.

FIG. 17 is an exploded perspective view of the particular embodiment of the connector shown in FIG. 16.

III. DETAILED DESCRIPTION OF THE PREFERRED EMBODIMENTS

Figure 1:
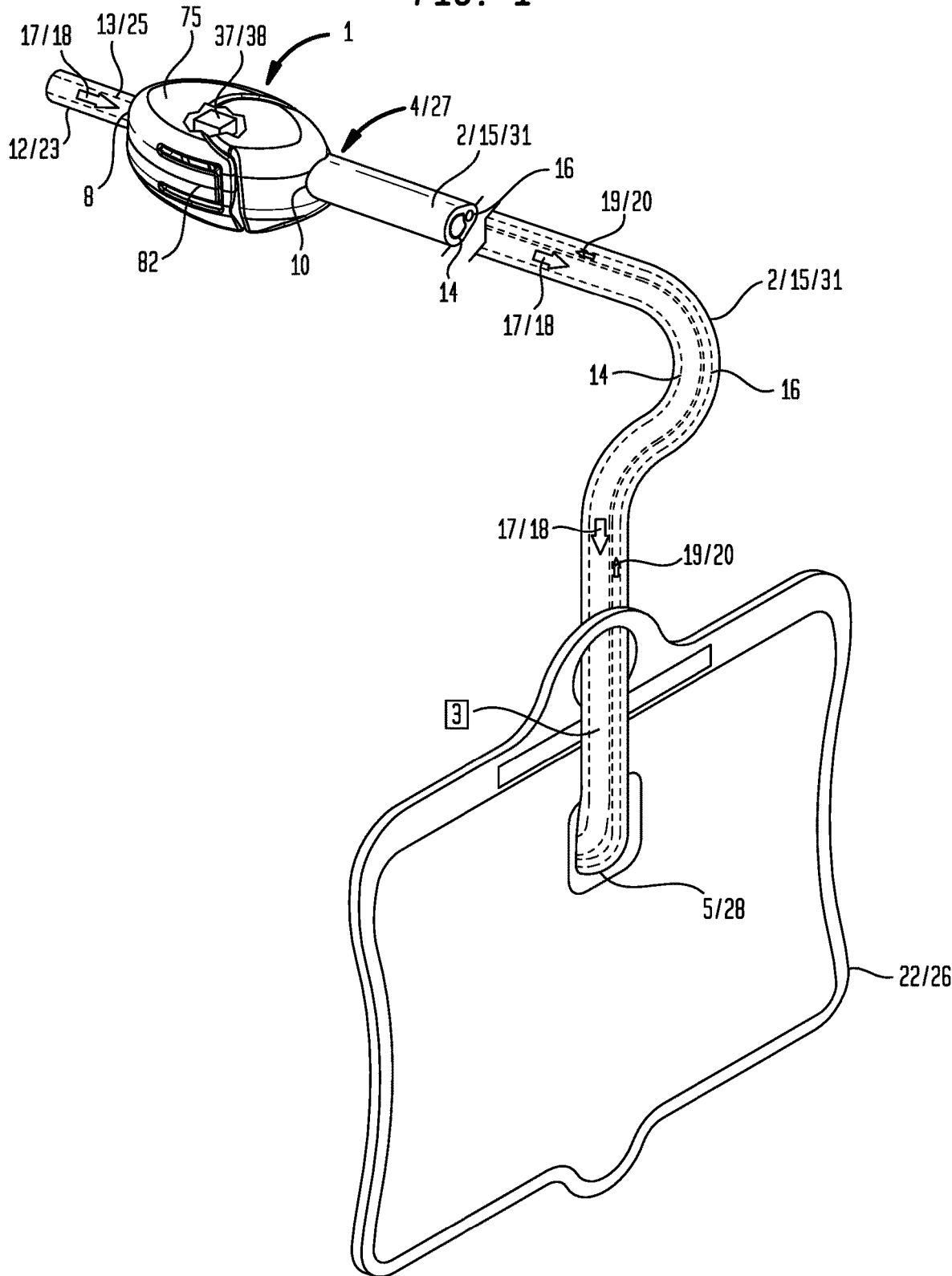
FIG. 1 is an illustration of a method of using a particular embodiment of the connector system which couples to an outlet conduit to decrease an outlet conduit passageway pressure differential between outlet conduit opposing first and second ends and/or for sensing a parameter of a first fluid flowing in a first fluid flow path through a connector passageway.

Now referring primarily to FIG. 1, which illustrates a method of using a particular embodiment of an inventive connector (1) which couples to an outlet conduit (2) to decrease an outlet conduit passageway pressure differential (3) between outlet conduit opposing first and second ends (4)(5), whereby the connector (1) includes a mixing chamber (6) having a first inlet port (7) in fluidic communication with a connector first open end (8) and the mixing chamber (6); an outlet port (9) in fluidic communication with the mixing chamber (6) and a connector second open end (10); and a second inlet port (11) in fluidic communication with the connector second open end (10) and the mixing chamber (6).

The method includes coupling a first inlet conduit (12) to the connector first open end (8) to fluidicly couple a first inlet conduit passageway (13) with the first inlet port (7), coupling the outlet conduit (2) to the connector second open end (10) to fluidicly couple an outlet conduit passageway (14) with the outlet port (9), and coupling a second inlet conduit (15) to the connector second open end (10) to fluidicly couple a second inlet conduit passageway (16) with the second inlet port (11).

As to particular embodiments, the method further includes generating a flow of a first fluid (17) in a first fluid flow path (18) defined by the first inlet conduit passageway (13), the first inlet port (7), the mixing chamber (6), the outlet port (9), and the outlet conduit passageway (14) (for example, from the first inlet conduit passageway (13) toward the outlet conduit passageway (14)); and generating a flow of a second fluid (19) in a second fluid flow path (20) defined by the second inlet conduit passageway (16), the second inlet port (11), and the mixing chamber (6) (for example, from the second inlet conduit passageway (16) toward the mixing chamber (6)). Within the mixing chamber (6), the second fluid (19) mixes with the first fluid (17) to decrease the outlet conduit passageway pressure differential (3) between the outlet conduit opposing first and second ends (4)(5).

Now referring primarily to FIG. 2 through FIG. 11, the connector (1) includes a mixing chamber (6) which, as to particular embodiments, can be defined by a connector internal surface (21) between connector first and second open ends (8)(10).

Figure 3:
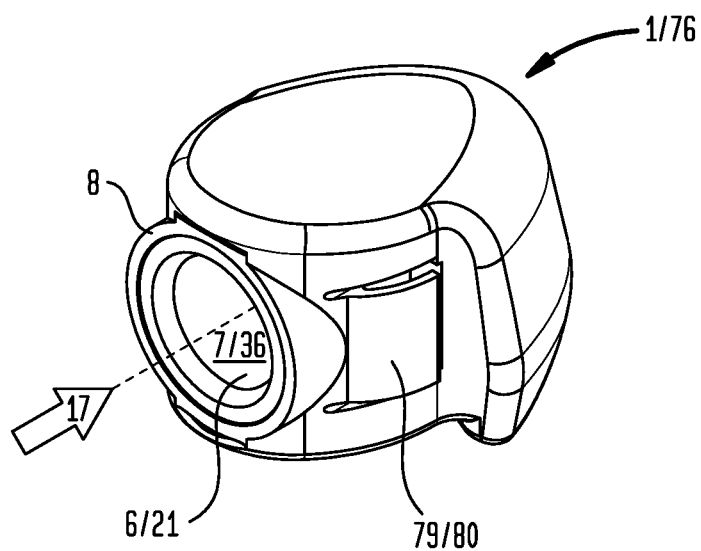
FIG. 3 is a perspective view of a particular embodiment of a connector (or a second housing of a connector) showing a connector first open end.
Figure 4:
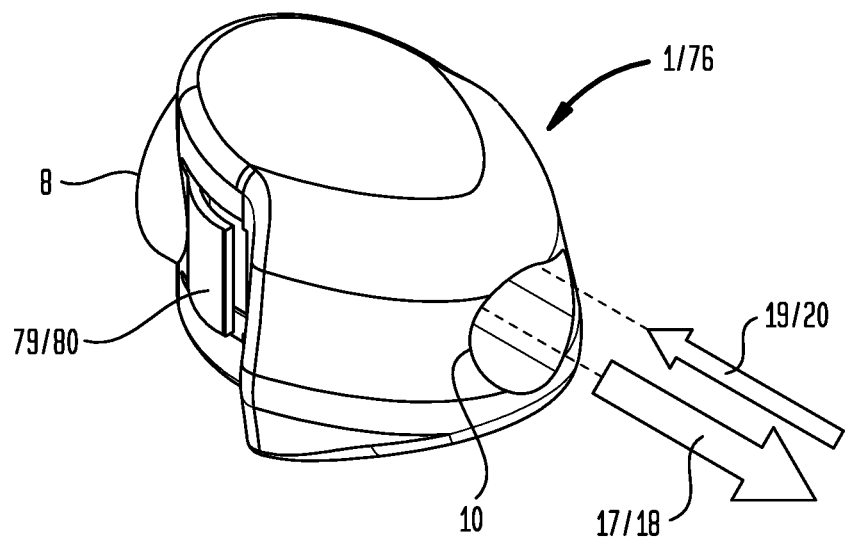
FIG. 4 is a perspective view of a particular embodiment of a connector (or a second housing of a connector) showing a connector second open end.
Figure 5:
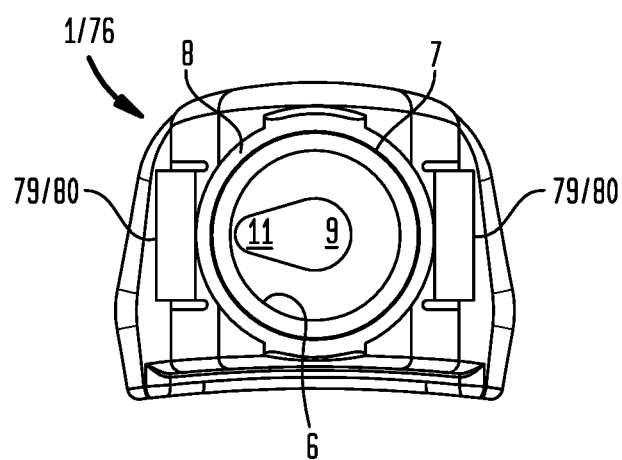
FIG. 5 is a first end view of a particular embodiment of a connector (or a second housing of a connector).

Now referring primarily to FIG. 3 and FIG. 5, the mixing chamber (6) includes a first inlet port (7) in fluidic communication with the connector first open end (8) and the mixing chamber (6). Accordingly, a first fluid (17) can ingress into the mixing chamber (6) from the connector first open end (8) by flowing through the first inlet port (7), whereby as to particular embodiments, the first fluid (17) can be a liquid.

Figure 6:
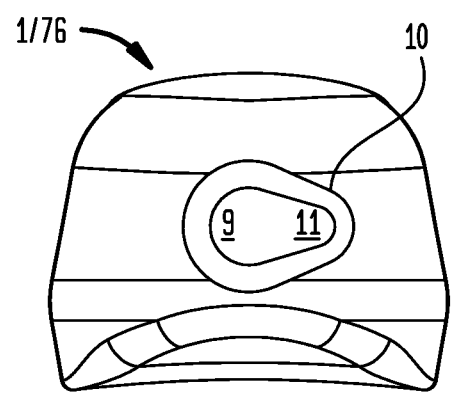
FIG. 6 is a second end view of a particular embodiment of a connector (or a second housing of a connector).
Figure 7:
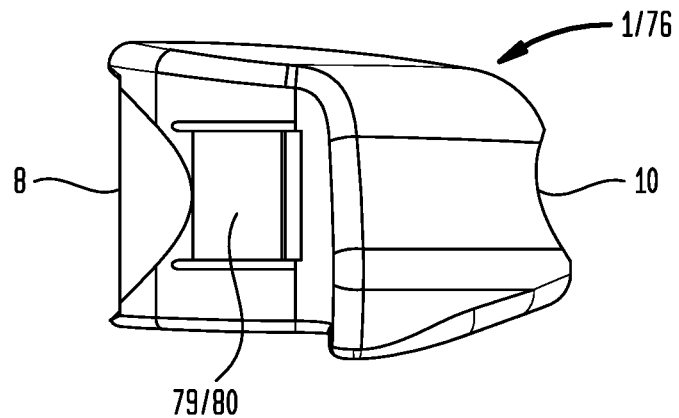
FIG. 7 is a first side view of a particular embodiment of a connector (or a second housing of a connector).
Figure 8:
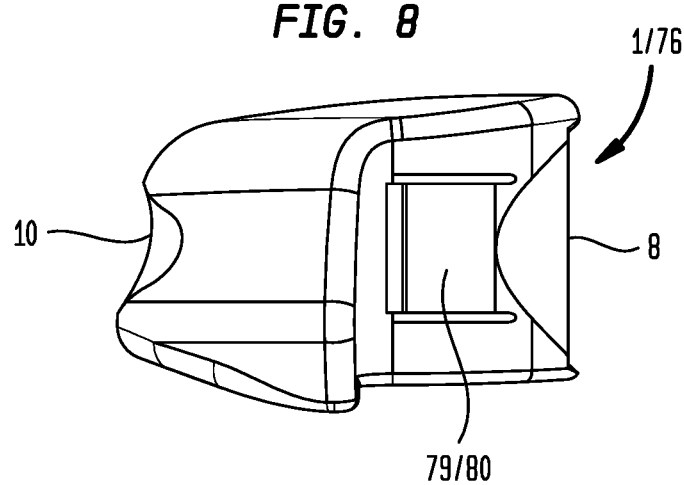
FIG. 8 is a second side view of a particular embodiment of a connector (or a second housing of a connector).
Figure 9:
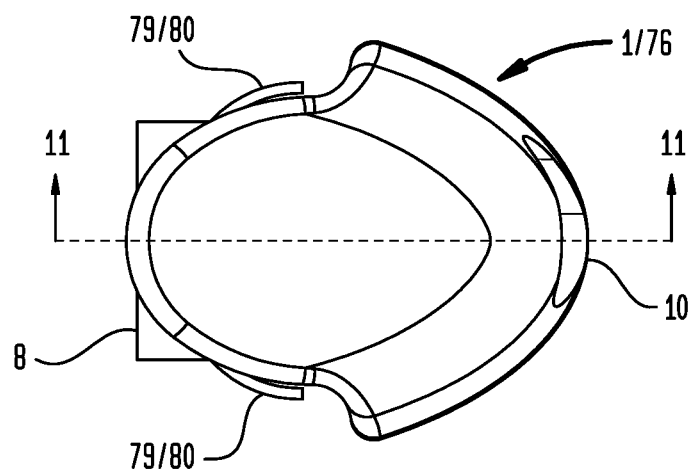
FIG. 9 is a top view of a particular embodiment of a connector (or a second housing of a connector).
Figure 10:
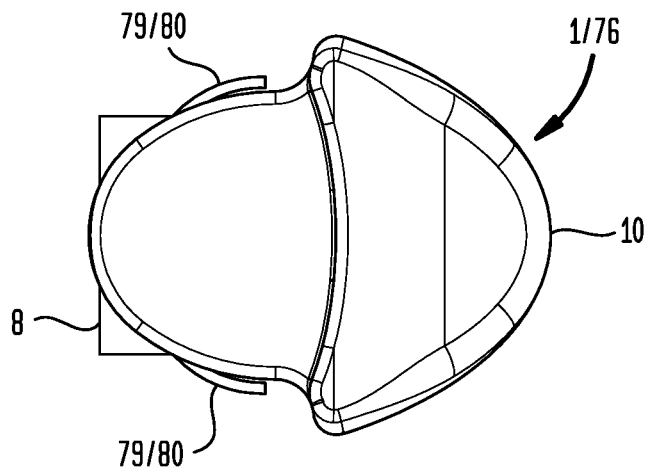
FIG. 10 is a bottom view of a particular embodiment of a connector (or a second housing of a connector).
Figure 11:
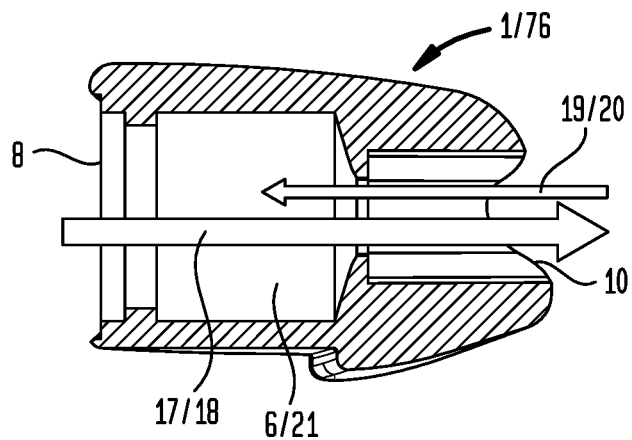
FIG. 11 is a cross-sectional view of the particular embodiment of the connector shown in FIG. 9.

Now referring primarily to FIG. 5 and FIG. 6, the mixing chamber (6) further includes an outlet port (9) in fluidic communication with the mixing chamber (6) and the connector second open end (10). Accordingly, the first fluid (17) can egress from the mixing chamber (6) toward the connector second open end (0) by flowing through the outlet port (9).

Correspondingly, a first fluid flow path (18) can be defined by the connector first open end (8), the first inlet port (7), the mixing chamber (6), the outlet port (9), and the connector second open end (10), whereby as to particular embodiments, the first fluid (17) can flow from the connector first open end (8), through the mixing chamber (6), and toward the connector second open end (10) (as shown in the example of FIG. 12).

Figure 2:
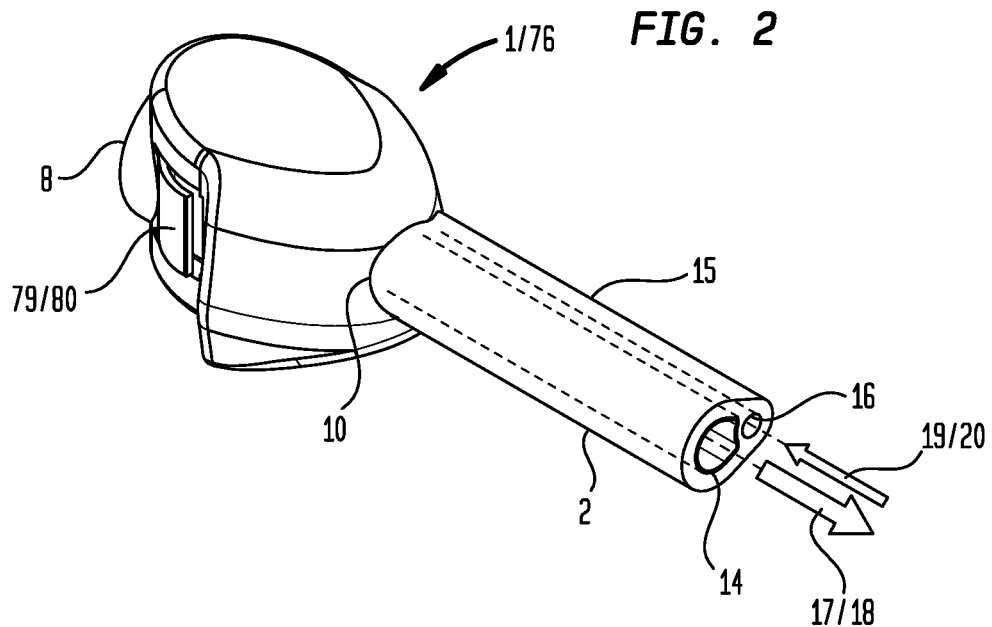
FIG. 2 is a perspective view of a particular embodiment of a connector (or a second housing of a connector) having an outlet conduit and a second inlet conduit coupled to a connector second open end.

Now referring primarily to FIG. 2, FIG. 16, and FIG. 17, the connector first open end (8) can be configured to couple to a first inlet conduit (12) to fluidicly couple a first inlet conduit passageway (13) with the first inlet port (7) and the connector second open end (10) can be configured to couple to an outlet conduit (2) to fluidicly couple an outlet conduit passageway (14) with the outlet port (9).

As but one illustrative example, the first inlet conduit (12) and the outlet conduit (2) can be received within the corresponding connector first and second open ends (8)(10) to sealably engage the first inlet conduit (12) and the outlet conduit (2) with the corresponding connector first and second open ends (8)(10) and fluidicly couple the first inlet conduit passageway (13) and the outlet conduit passageway (14) with the corresponding first inlet port (7) and outlet port (9).

As another illustrative example, the first inlet conduit (12) and the outlet conduit (2) can be disposed around the corresponding connector first and second open ends (8)(10) to sealably engage the first inlet conduit (12) and the outlet conduit (2) with the corresponding connector first and second open ends (8)(10) and fluidicly couple the first inlet conduit passageway (13) and the outlet conduit passageway (14) with the corresponding first inlet port (7) and outlet port (9).

Now referring primarily to FIG. 16 and FIG. 17, upon coupling of the first inlet conduit (12) and the outlet conduit (2) to the corresponding connector first and second open ends (8)(10), the first fluid flow path (18) can be defined by the first inlet conduit passageway (13), the first inlet port (7), the mixing chamber (6), the outlet port (9), and the outlet conduit passageway (14), whereby as to particular embodiments, the first fluid (17) can flow from the first inlet conduit passageway (13), through the mixing chamber (6), and toward the outlet conduit passageway (14).

Now referring primarily to FIG. 1, the outlet conduit (2) has outlet conduit opposing first and second ends (4)(5), in between which the outlet conduit passageway (14) is disposed. The outlet conduit first end (4) can couple to the connector second open end (10) and the outlet conduit second end (5) can couple to a collection reservoir (22) to fluidicly couple the mixing chamber (6) with the collection reservoir (22) via the outlet conduit passageway (14). Subsequently, as to particular embodiments, the first fluid (17) can flow in the first fluid flow path (18) from the first inlet conduit passageway (13), through the mixing chamber (6) and the outlet conduit passageway (14), and into the collection reservoir (22), generating a closed fluid flow path between the first inlet conduit passageway (13) and the collection reservoir (22).

For the purposes of the present invention, the term "closed fluid flow path" means a fluid flow path in which mass does not transfer into or out of.

Following, as the first fluid (17) is collected within the collection reservoir (22), an outlet conduit passageway pressure differential (3) between the outlet conduit opposing first and second ends (4)(5) can be generated. As such, a greater pressure (or positive pressure) can be generated within the outlet conduit passageway (14) proximate the outlet conduit second end (5) relative to the outlet conduit first end (4), whereby the greater pressure can inhibit, either partially or completely, the flow of the first fluid (17) into the collection reservoir (22).

As but one illustrative example, the first inlet conduit (12) can be configured as a catheter (23) having a catheter first end coupled to a bladder of a user (not shown) and a catheter second end coupled to the connector first open end (8), fluidicly coupling the bladder with the mixing chamber (6) via a catheter passageway (25) between the catheter first end and the catheter second ends. The outlet conduit (2) can have an outlet conduit first end (4) coupled to the connector second open end (10) and an outlet conduit second end (5) coupled to a collection reservoir (22) configured as a urine drainage bag (26), fluidicly coupling the mixing chamber (6) with the urine drainage bag (26) via the outlet conduit passageway (14). Accordingly, the first fluid (17), which can be urine, can flow in the closed fluid flow path from the bladder to the urine drainage bag (26). However, upon collection of an amount of urine within the urine drainage bag (26), a greater pressure can be generated within the outlet conduit passageway (14) proximate the outlet conduit second end (5) relative to the outlet conduit first end (4). In addition to potentially inhibiting, either partially or completely, the flow of urine from the bladder to the urine drainage bag (26), the greater pressure may also cause discomfort or pain to the user.

Therefore, the mixing chamber (6) further includes a second inlet port (11) in fluidic communication with the connector second open end (10) and the mixing chamber (6). Accordingly, a second fluid (19) can ingress into the mixing chamber (6) from the connector second open end (10) by flowing through the second inlet port (11), whereby as to particular embodiments, the second fluid (19) can be a gas.

Correspondingly, a second fluid flow path (20) can be defined by the connector second open end (10), the second inlet port (11), and the mixing chamber (6), whereby as to particular embodiments, the second fluid (19) can flow from the connector second open end (10) toward the mixing chamber (6).

Now referring primarily to FIG. 2, FIG. 16, and FIG. 17, the connector second open end (10) can further be configured to couple to a second inlet conduit (15) to fluidicly couple a second inlet conduit passageway (16) with the second inlet port (11).

Again referring primarily to FIG. 2, FIG. 16, and FIG. 17, upon coupling of the second inlet conduit (15) to the connector second open end (10), the second fluid flow path (20) can be defined by the second inlet conduit passageway (16), the second inlet port (11), and the mixing chamber (6), whereby as to particular embodiments, the second fluid (19) can flow from the second inlet conduit passageway (16) toward the mixing chamber (6).

Now referring primarily to FIG. 1, the second inlet conduit (15) has second inlet conduit opposing first and second ends (27)(28), in between which the second inlet conduit passageway (16) is disposed. The second inlet conduit first end (27) can couple to the connector second open end (10) and the second inlet conduit second end (28) can couple to the collection reservoir (22) to fluidicly couple the collection reservoir (22) to the mixing chamber (6) via the second inlet conduit passageway (16). Subsequently, as to particular embodiments, the second fluid (19) can flow in the second fluid flow path (20) from the collection reservoir (22), through the second inlet conduit passageway (16), and into the mixing chamber (6), adding to the closed fluid flow path between the first inlet conduit passageway (13) and the collection reservoir (22).

Following, as the first fluid (17) is collected within the collection reservoir (22) and an outlet conduit passageway pressure differential (3) between the outlet conduit opposing first and second ends (4)(5) is generated, as to particular embodiments, the second fluid (19) can flow in the second fluid flow path (20) from the second inlet conduit passageway (16) toward the mixing chamber (6). Within the mixing chamber (6), the second fluid (19) mixes with the first fluid (17) to decrease the outlet conduit passageway pressure differential (3) between the outlet conduit opposing first and second ends (4)(5).

Regarding the illustrative example whereby the first inlet conduit (12) is configured as a catheter (23) coupled between a bladder of a user and the connector first open end (8), and the outlet conduit (2) couples between the connector second end (10) and a urine drainage bag (26), urine can flow in the closed fluid flow path from the bladder to the urine drainage bag (26). Upon collection of an amount of urine within the urine drainage bag (26), the second fluid (19), such as gas from a headspace of the urine drainage bag (26), can flow in the second fluid flow path (20) from the collection reservoir (22), through the second inlet conduit passageway (16), and into the mixing chamber (6), in which the second fluid (19) can mix with the urine to decrease the outlet conduit passageway pressure differential (3) between the outlet conduit opposing first and second ends (4)(5). Hence, upon collection of the urine within the urine drainage bag (26), a significant outlet conduit passageway pressure differential (3) may not be generated and, consequently, the flow of urine from the bladder to the urine drainage bag (26) may not be inhibited.

As to particular embodiments, when flowing in the second fluid flow path (20), the second fluid (19) can urge the first fluid (17) through the outlet port (9) and into the outlet conduit passageway (14), thereby facilitating flow of the first fluid (17) in the first fluid flow path (18).

Figure 12A:
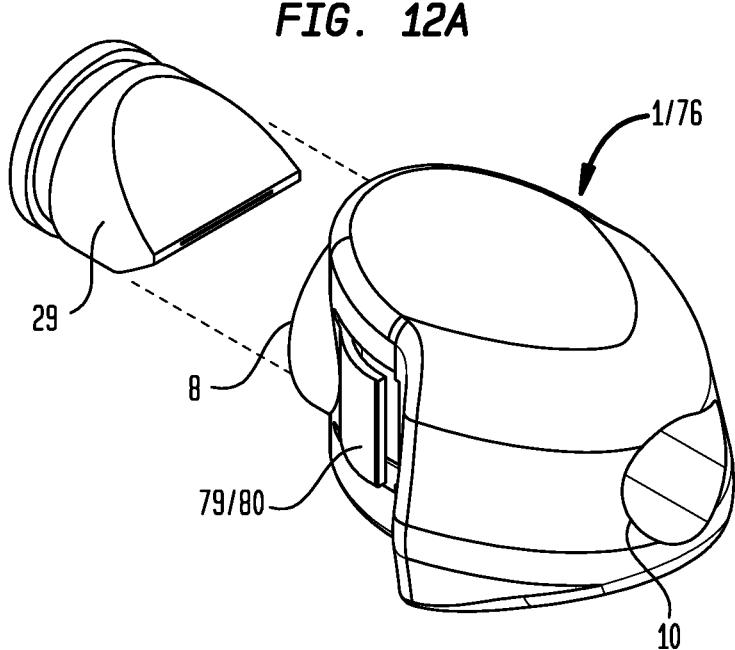
FIG. 12A is an exploded perspective view of a particular embodiment of a connector (or a second housing of a connector) and a first valve.
Figure 12B:
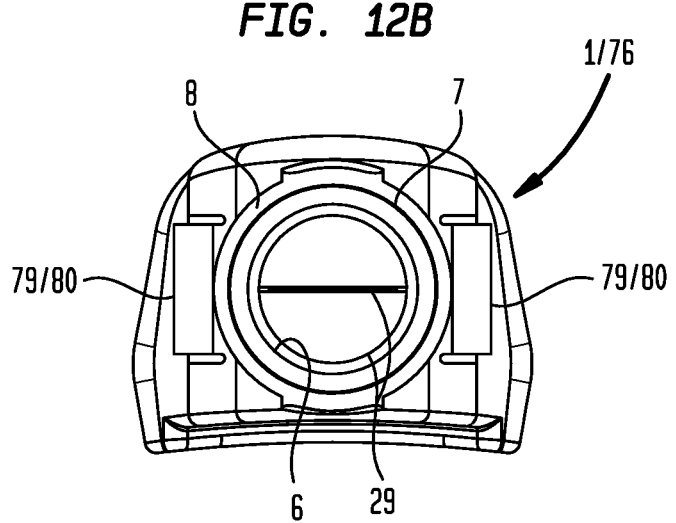
FIG. 12B is a first end view of a particular embodiment of a connector (or a second housing of a connector) with a first valve disposed within a connector first open end.
Figure 13:
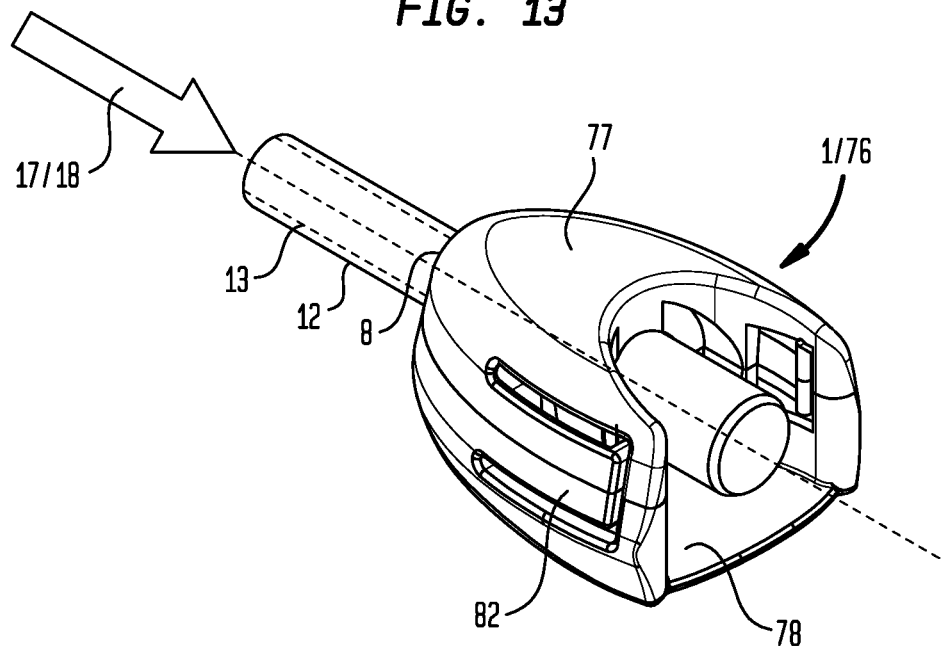
FIG. 13 is a perspective view of a particular embodiment of a first housing of a connector having a first inlet conduit coupled to a connector first open end.
Figure 14:
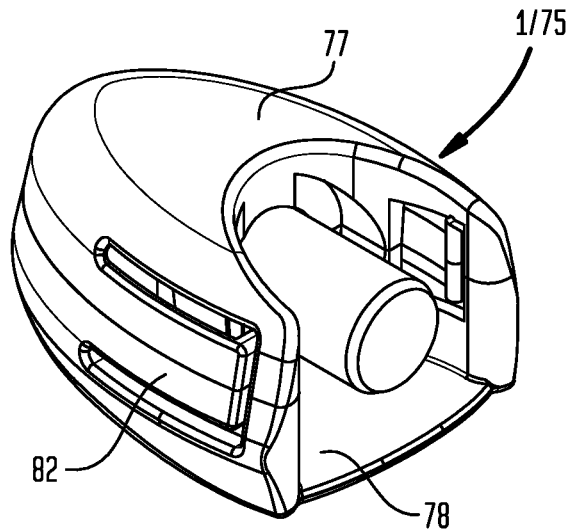
FIG. 14 is a perspective view of a particular embodiment of a first housing of a connector.
Figure 15:
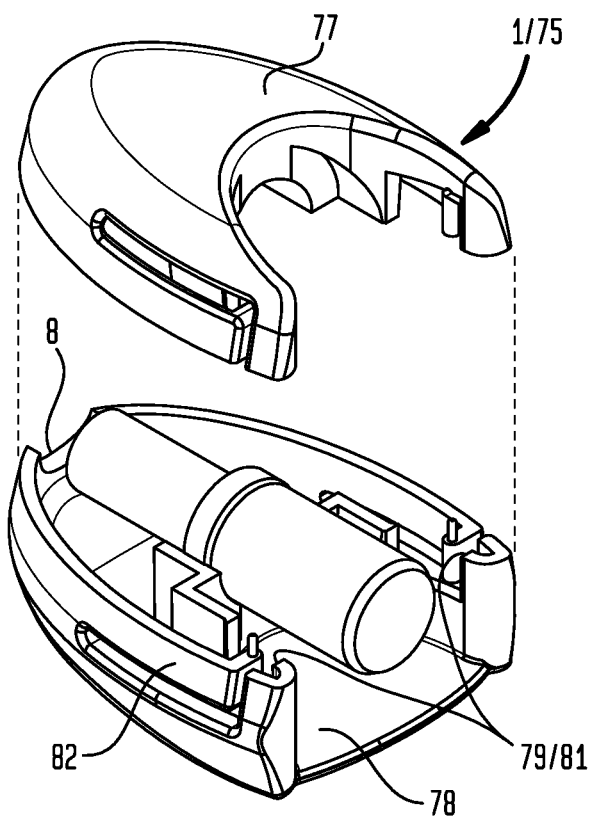
FIG. 15 is an exploded perspective view of a particular embodiment of a first housing of a connector having first housing upper and lower portions.
Figure 18:
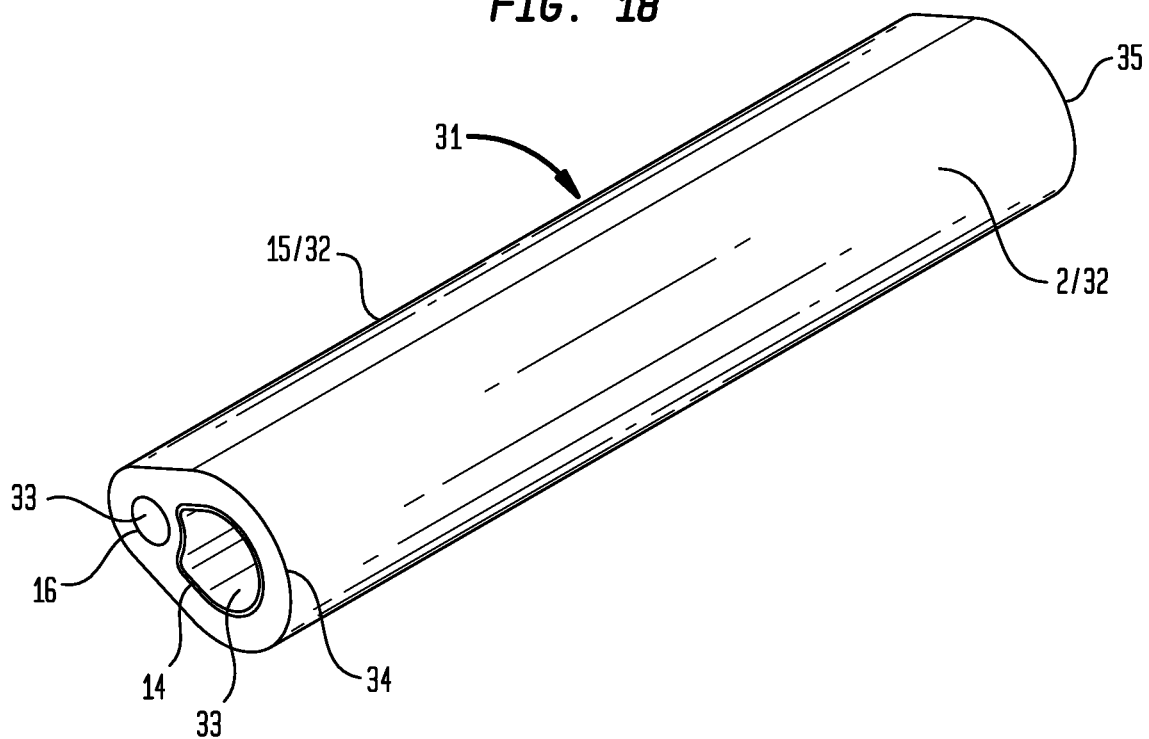
FIG. 18 is a perspective view of a particular embodiment of an outlet conduit and a second inlet conduit combined into a one-piece tubular construct including both an outlet conduit passageway and a second inlet conduit passageway.

Now referring primarily to FIG. 12A and FIG. 12B, the connector (1) can, but need not necessarily, further include a first valve (29) disposed within the first fluid flow path (18) to regulate flow of the first fluid (17). As to particular embodiments, the first valve (29) can be a unidirectional first valve (29) configured to allow a first directional flow of the first fluid (17) from the connector first open end (8) toward the connector second open end (10). Correspondingly, the unidirectional first valve (29) interrupts a second directional flow of the first fluid (17) from the connector second open end (10) toward the connector first open end (8).

Thus, upon coupling of the first inlet conduit (12) and the outlet conduit (2) to the corresponding connector first and second open ends (8)(10), the first fluid flow path (18), defined by the first inlet conduit passageway (13), the first inlet port (7), the mixing chamber (6), the outlet port (9), and the outlet conduit passageway (14), can be a unidirectional fluid flow path, whereby the first fluid (17) flows only from the first inlet conduit passageway (13) toward the outlet conduit passageway (14).

The unidirectional first valve (29) can have any type of valve configuration capable of regulating flow of the first fluid (17) as described herein and, without limitation to the breadth of the foregoing, can include as illustrative examples: a duckbill valve, a flapper valve, an umbrella valve, a spring-loaded valve, or any of a numerous and wide variety of valve configurations as would be known to one of ordinary skill in the art as capable of unidirectionally regulating a fluid flow.

Figure 19:
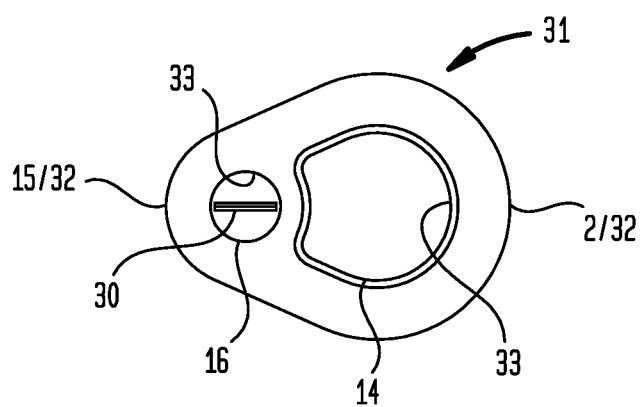
FIG. 19 is an end view of the particular embodiment of the one-piece tubular construct shown in FIG. 18, including a second valve disposed within a second fluid flow path to regulate flow of a second fluid.
Figure 20:
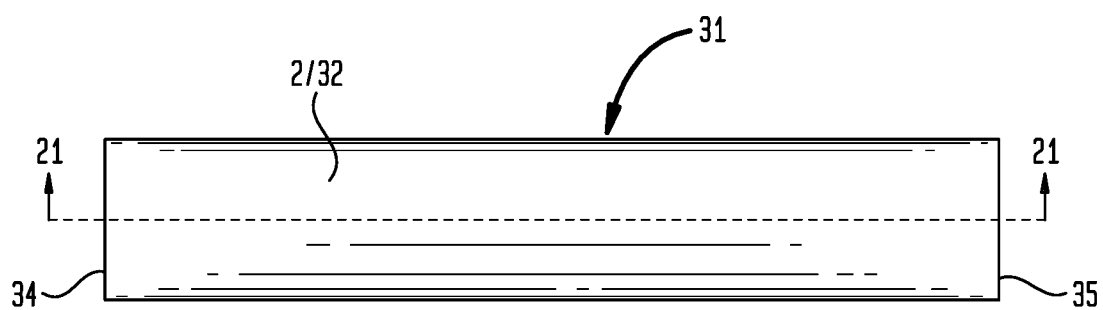
FIG. 20 is a top view of the particular embodiment of the one-piece tubular construct shown in FIG. 18, including a second valve disposed within a second fluid flow path to regulate flow of a second fluid.
Figure 21:
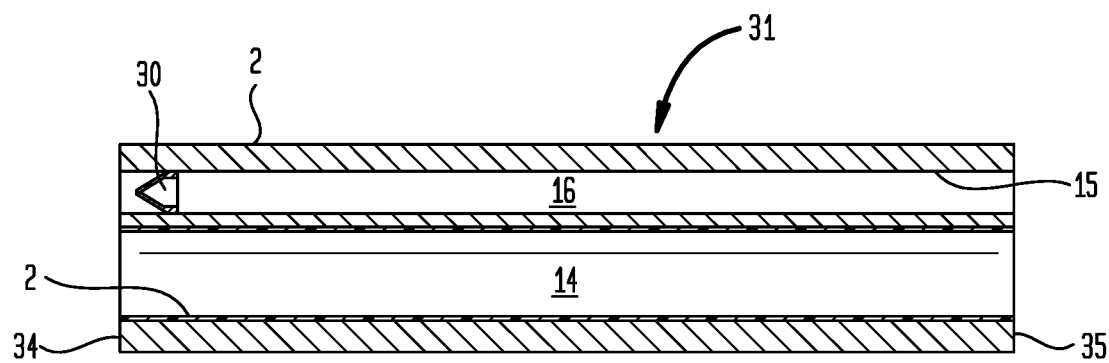
FIG. 21 is a cross-sectional view of the particular embodiment of the one-piece tubular construct shown in FIG. 20.

Now referring primarily to FIG. 19 through FIG. 21, the connector (1) can, but need not necessarily, further include a second valve (30) disposed within the second fluid flow path (20) to regulate flow of the second fluid (19). As to particular embodiments, the second valve (30) can be a unidirectional second valve (30) configured to allow a first directional flow of the second fluid (19) from the connector second open end (10) toward the mixing chamber (6). Correspondingly, the unidirectional second valve (30) interrupts a second directional flow of the second fluid (19) from the mixing chamber (6) toward the connector second open end (10).

Thus, upon coupling of the second inlet conduit (15) to the connector second open end (10), the second fluid flow path (20), defined by the second inlet conduit passageway (16), the second inlet port (11), and the mixing chamber (6), can be a unidirectional fluid flow path, whereby the second fluid (30) flows only from the second inlet conduit passageway (16) toward the mixing chamber (6).

The unidirectional second valve (30) can have any type of valve configuration capable of regulating flow of the second fluid (19) as described herein and, without limitation to the breadth of the foregoing, can include as illustrative examples: a duckbill valve, a flapper valve, an umbrella valve, a spring-loaded valve, or any of a numerous and wide variety of valve configurations as would be known to one of ordinary skill in the art as capable of unidirectionally regulating a fluid flow.

As to particular embodiments, the unidirectional second valve (30) can be coupled or connected to the connector internal surface (21) to dispose the unidirectional second valve (30) within the second fluid flow path (20) (not shown).

As to other particular embodiments, the unidirectional second valve (30) can be disposed within the second inlet conduit passageway (16) to dispose the unidirectional second valve (30) within the second fluid flow path (20) (as shown in the examples of the Figures).

As to particular embodiments, the outlet conduit (2) having the outlet conduit passageway (14) can be discrete from the second inlet conduit (15) having the second inlet conduit passageway (16) (not shown).

Now referring primarily to FIG. 2, FIG. 16, FIG. 17, and FIG. 18 through FIG. 21, as to other particular embodiments, the outlet conduit (2) and the second inlet conduit (15) can be combined into a one-piece tubular construct (31) including both the outlet conduit passageway (14) and the second inlet conduit passageway (16).

The one-piece tubular construct (31) can have one-piece tubular construct opposing external and internal surfaces (32)(33) disposed between one-piece tubular construct opposing first and second ends (34)(35), whereby the one-piece tubular construct internal surface (33) can define a discrete outlet conduit passageway (14) and a discrete second inlet conduit passageway (16), both of which communicate between the one-piece tubular construct opposing first and second ends (34)(35).

As to particular embodiments, the outlet conduit passageway (14) and the second inlet conduit passageway (16) can dispose in laterally adjacent relation to one another between the one-piece tubular conduit opposing first and second ends (34)(35) (as shown in the examples of the Figures).

As to other particular embodiments, the outlet conduit passageway (14) and the second inlet conduit passageway (16) can dispose in concentric relation to one another between the one-piece tubular conduit opposing first and second ends (34)(35) (not shown).

Now referring primarily to FIG. 1, which illustrates a method of using another particular embodiment of an inventive connector (1) for sensing a parameter of a first fluid (17) flowing in a first fluid flow path (18) through a connector passageway (36), whereby the connector (1) includes a connector internal surface (21) defining a connector passageway (36) which communicates between connector first and second open ends (8)(10); and a sensor module (37) operatively coupled to the connector passageway (36). The method includes generating a flow of the first fluid (17) in the first fluid flow path (18) through the connector passageway (36), and sensing the parameter of the first fluid (17) flowing in the first fluid flow path (18) through the connector passageway (36).

Now referring primarily to FIG. 3, the connector (1) includes a connector internal surface (21) defining a connector passageway (36) which communicates between connector first and second open ends (8)(10).

Correspondingly, a first fluid flow path (18) can be defined by the connector first open end (8), the connector passageway (36), and the connector second open end (10), whereby as to particular embodiments, the first fluid (17) flows from the connector first open end (8), through the connector passageway (36), and toward the connector second open end (10).

Now referring primarily to FIG. 2, FIG. 16, and FIG. 17, the connector first open end (8) can be configured to couple to a first inlet conduit (12) to fluidicly couple a first inlet conduit passageway (13) with the connector passageway (36), and the connector second open end (10) can be configured to couple to an outlet conduit (2) to fluidicly couple an outlet conduit passageway (14) with the connector passageway (36).

As but one illustrative example, the first inlet conduit (12) and the outlet conduit (2) can be received within the corresponding connector first and second open ends (8)(10) to sealably engage the first inlet conduit (12) and the outlet conduit (2) with the corresponding connector first and second open ends (8)(10) and fluidicly couple the first inlet conduit passageway (13) and the outlet conduit passageway (14) with the connector passageway (36).

As another illustrative example, the first inlet conduit (12) and the outlet conduit (2) can be disposed around the corresponding connector first and second open ends (8)(10) to sealably engage the first inlet conduit (12) and the outlet conduit (2) with the corresponding connector first and second open ends (8)(10) and fluidicly couple the first inlet conduit passageway (13) and the outlet conduit passageway (14) with the connector passageway (36).

Now referring primarily to FIG. 16 and FIG. 17, upon coupling of the first inlet conduit (14) and the outlet conduit (2) to the corresponding connector first and second open ends (8)(10), the first fluid flow path (18) can be defined by the first inlet conduit passageway (13), the connector passageway (36), and the outlet conduit passageway (14).

Now referring primarily to FIG. 12A and FIG. 12B, the connector (1) can, but need not necessarily, further include a first valve (29) disposed within the first fluid flow path (18) to regulate flow of the first fluid (17). As to particular embodiments, the first valve (29) can be a unidirectional first valve (29) configured to allow a first directional flow of the first fluid (17) from the connector first open end (8) toward the connector second open end (10). Correspondingly, the unidirectional first valve (29) interrupts a second directional flow of the first fluid (17) from the connector second open end (10) toward the connector first open end (8).

Thus, upon coupling of the first inlet conduit (12) and the outlet conduit (2) to the corresponding connector first and second open ends (8)(10), the first fluid flow path (18), defined by the first inlet conduit passageway (13), the connector passageway (36), and the outlet conduit passageway (14), can be a unidirectional fluid flow path, whereby the first fluid (17) flows only from the first inlet conduit passageway (13) toward the outlet conduit passageway (14).

The unidirectional first valve (29) can have any type of valve configuration capable of regulating flow of the first fluid (17) as described herein and, without limitation to the breadth of the foregoing, can include as illustrative examples: a duckbill valve, a flapper valve, an umbrella valve, a spring-loaded valve, or any of a numerous and wide variety of valve configurations as would be known to one of ordinary skill in the art as capable of unidirectionally regulating a fluid flow.

Figure 22:
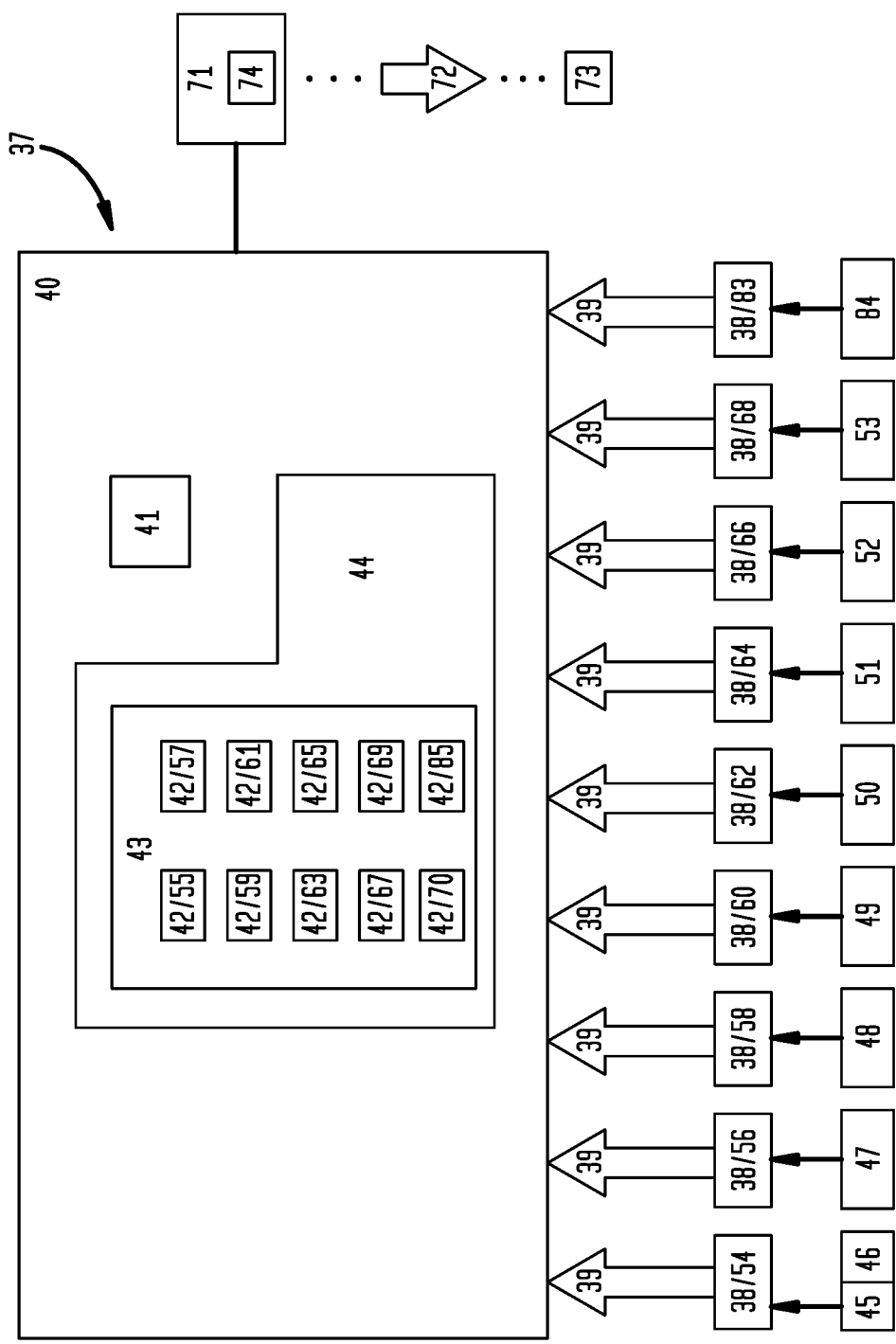
FIG. 22 is an illustration of a particular embodiment of a sensor module of the connector.

Now referring primarily to FIG. 22, the connector (1) further includes a sensor module (37) operatively coupled to the connector passageway (36) to sense a parameter of a first fluid (17) flowing in a first fluid flow path (18) through the connector passageway (36).

Again referring primarily to FIG. 22, the sensor module (37) can include one or more sensors (38) which each generate a sensor signal (39). The sensor module (37) can further include a microcontroller (40) configured to receive, process, and transform each sensor signal (39).

The microcontroller (40) can take the form of a small computer on one or more integrated circuits, whereby the microcontroller (40) can include at least one processor (41) which operatively controls the function of a variety of modules (42) stored as computer program code (43) in a programmable memory element (44), whereby each module (42) functions to provide a response related to the sensor signal (39) received by the microcontroller (40). A bus can operably couple components of the microcontroller (40), including without limitation, the processor (41) and the programmable memory element (44).

The microcontroller (40) can be a conventional microcontroller (40). As an illustrative example, a microcontroller (40) suitable for use with embodiments of the connector (1) can be obtained from Microchip Technology Inc., 2355 West Chandler Boulevard, Chandler, Ariz. 85224, USA, for example Part Numbers PIC18F4620-I/PT, PIC18LF14K22, or PIC18LF15K22. However, the invention need not be so limited, as any of a numerous and wide variety of similar or equivalent components can be suitable as a microcontroller (40) programmable to perform the functions of the connector (1) as described or shown herein.

The processor (41) can include one central-processing unit (CPU), a plurality of processors which operate in parallel to process digital information, a digital signal processor (DSP) plus a host processor, or the like, or other conventional processors (41) as would be known to one of ordinary skill in the art.

The bus can include any bus configuration having any of a wide variety of bus architectures.

The programmable memory element (44) can be a read only memory (ROM) or a random access memory (RAM), or both, or other conventional memory elements (44) as would be known to one of ordinary skill in the art.

Again referring primarily to FIG. 22, the one or more sensors (38) can include any of a wide variety of sensors (38) which can sense various parameters of the first fluid (17) flowing in the first fluid flow path (18) through the connector passageway (36). As non-limiting examples, the sensed parameters can include fluid flow rate (45), fluid volume (46), fluid temperature (47), fluid pH (48), fluid conductivity (49), fluid turbidity (50), amount of blood in fluid (51), amount of protein in fluid (52), amount of dissolved gas in fluid (53), or the like, or combinations thereof, or any desired parameter of the first fluid (17) flowing in the first fluid flow path (18) through the connector passageway (36).

As to particular embodiments, the sensor (38) can be a fluid flow rate sensor (54) which can send a sensor signal (39) to a fluid flow rate calculation module (55) within the microcontroller (40). As to particular embodiments, the fluid flow rate sensor (54) can have a resistive element configured to maintain a constant temperature. When the first fluid (17) flowing in the first fluid flow path (18) through the connector passageway (36) has a fluid temperature lesser than the temperature which the resistive element is configured to maintain, an amount of heat transfers from the resistive element to the first fluid (17), thereby lessening the temperature of the resistive element below the temperature which the resistive element is configured to maintain. Accordingly, an amount of current is generated to increase the temperature of the resistive element toward the temperature which the resistive element is configured to maintain, whereby the amount of current required to increase the temperature can be related to the fluid flow rate of the first fluid (17) flowing in the first fluid flow path (18) through the connector passageway (36). As to particular embodiments, the fluid volume (46) can additionally be calculated.

As to particular embodiments, the sensor (38) can be a fluid temperature sensor (56) configured as a thermistor, a thermocouple, a thermostat, a semiconductor circuit, or the like, or other conventional temperature sensing devices as would be known to one of ordinary skill in the art. As an illustrative example, a suitable thermistor for use with embodiments of the connector (1) can be obtained from Microchip Technology Inc., 2355 West Chandler Boulevard, Chandler, Ariz. 85224, USA, for example Part Number MCP98242. However, the invention need not be so limited, as any of a numerous and wide variety of similar or equivalent components can be suitable as a fluid temperature sensor (56) configured to sense a fluid temperature (47) and send a corresponding sensor signal (39) to a fluid temperature module (57) within the microcontroller (40).

As to particular embodiments, the sensor (38) can be a fluid pH sensor (58), as would be known to one of ordinary skill in the art, which can sense the fluid pH (48) and send a corresponding sensor signal (39) to a fluid pH module (59) within the microcontroller (40).

As to particular embodiments, the sensor (38) can be a fluid conductivity sensor (60), as would be known to one of ordinary skill in the art, which can sense the fluid conductivity (49) and send a corresponding sensor signal (39) to a fluid conductivity module (61) within the microcontroller (40).

As to particular embodiments, the sensor (38) can be a fluid turbidity sensor (62), as would be known to one of ordinary skill in the art, which can sense the fluid turbidity (50) and send a corresponding sensor signal (39) to a fluid turbidity module (63) within the microcontroller (40).

As to particular embodiments, the sensor (38) can be a blood content sensor (64), as would be known to one of ordinary skill in the art, which can sense an amount of blood in the fluid (51) and send a corresponding sensor signal (39) to a blood content module (65) within the microcontroller (40).

As to particular embodiments, the sensor (38) can be a protein content sensor (66), as would be known to one of ordinary skill in the art, which can sense an amount of protein in the fluid (52) and send a corresponding sensor signal (39) to a protein content module (67) within the microcontroller (40).

As to particular embodiments, the sensor (38) can be a dissolved gas sensor (68), as would be known to one of ordinary skill in the art, which can sense an amount of dissolved gas in the fluid (53) and send a corresponding sensor signal (39) to a dissolved gas module (69) within the microcontroller (40).

As to particular embodiments, the sensor (38) can generate an analog sensor signal, which can be received by the microcontroller (40). As to particular embodiments, the sensor (38) can continuously or intermittently sense the parameter and correspondingly continuously or intermittently generate the sensor signal (39) receivable by the microcontroller (40). A sensor signal converter module (70) within the microcontroller (40) can convert the analog sensor signal into a digital sensor signal.

Now referring primarily to FIG. 22, the sensor module (37) can further include a transmitter (71) configured to transmit a transmitter signal (72) to a remote device (73), such as a computer. As to particular embodiments, the transmitter signal (72) can be transmitted over a local area network (LAN) or a wide area network (WAN) using conventional wired formats, such as Ethernet, or conventional wireless formats, such as wireless fidelity (Wi-Fi) digital communications protocols, which can be facilitated by an antenna (74).

It should be appreciated that the sensor module (37), including the sensors ( ), may be provided by any of a number of hardware of software components configured to performed the functions described herein.

Now referring primarily to FIG. 16 and FIG. 17, the connector (1), whether the connector (1) which couples to the outlet conduit (2) to decrease the outlet conduit passageway pressure differential (3) between outlet conduit opposing first and second ends (4)(5) or the connector (1) which senses a parameter of a first fluid (17) flowing in a first fluid flow path (38) through a connector passageway (36), can include discrete first and second housings (75)(76), whereby the first housing (75) defines the connector first open end (8) and the second housing (76) defines the connector second open end (10).

Again referring primarily to FIG. 16 and FIG. 17, as to particular embodiments, the first housing (75) can include first housing upper and lower portions (77)(78) which can matably engage with one another to provide an assembled first housing (75) which defines the connector first open end (8).

Again referring primarily to FIG. 16 and FIG. 17, as to particular embodiments, the first and second housings (75)(76) can releasably matably engage with one other to provide the first fluid flow path (18) between the connector first and second open ends (8)(10).

Again referring primarily to FIG. 16 and FIG. 17, as to particular embodiments, the first and second housings (75)(76) can include a latch assembly (79) which facilitates releasable matable engagement of the first and second housings (75)(76). The latch assembly (79) can include a latch (80) coupled to one of the first and second housings (75)(76) and a latch catch (81) coupled to the other of the first and second housings (75)(76), whereby the latch (80) can releasably matably engage with the latch catch (81) to facilitate releasable matable engagement of the first and second housings (75)(76).

Again referring primarily to FIG. 16 and FIG. 17, as but one illustrative example, the latch assembly (79) can include a pair of latches (80) which outwardly extend one each from opposing sides of the second housing (76). The latch assembly (79) further includes a corresponding pair of latch catches (81) which inwardly extend one each from opposing sides of the first housing (75). When the first and second housings (75)(76) are axially urged toward one another, the pair of latches (80) can releasably matably engage with the corresponding pair of latch catches (81) to facilitate releasable matable engagement of the first and second housings (75)(76).

Again referring primarily to FIG. 16 and FIG. 17, each latch (80) can be disengaged from the corresponding latch catch (81) by forcible urging upon a corresponding release element (82). As to particular embodiments, a pair of release elements (82) can be coupled one each to opposing sides of the first housing (75) proximate the pair of latch catches (81). Upon forcible inward urging, each release element (82) can function to inwardly urge the corresponding latch (80) to disengage the latch (80) from the corresponding latch catch (81). As such, the first and second housings (75)(76) can be disengaged from one another.

As can be easily understood from the foregoing, the basic concepts of the present invention may be embodied in a variety of ways. The invention involves numerous and varied embodiments of a connector system and methods for making and using such a connector system, including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "flow" should be understood to encompass disclosure of the act of "flowing"—whether explicitly discussed or not—and, conversely, were there effectively disclosure of the act of "flowing", such a disclosure should be understood to encompass disclosure of a "flow" and even a "means for flowing." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the connector systems herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application, if any, provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A method of making a connector which couples to an outlet conduit to decrease an outlet conduit passageway pressure differential between outlet conduit opposing first and second ends, said method comprising:
    providing a mixing chamber;
    fluidicly coupling a first inlet port with a connector first open end and said mixing chamber;
        wherein said connector first open end includes only one port, said port being said first inlet port;
    fluidicly coupling an outlet port with said mixing chamber and a connector second open end; and
    fluidicly coupling a second inlet port with said connector second open end and said mixing chamber;
    wherein said connector first open end is configured to couple to a first inlet conduit to fluidicly couple a first inlet conduit passageway to said first inlet port;
    wherein said connector second open end is configured to couple to an outlet conduit to fluidicly couple an outlet conduit passageway to said outlet port; and
    wherein said connector second open end is further configured to couple to a second inlet conduit to fluidicly couple a second inlet conduit passageway to said second inlet port.

2. The method of claim 1,
    wherein said first inlet conduit passageway, said first inlet port, said mixing chamber, said outlet port, and said outlet conduit passageway define a first fluid flow path in which a first fluid flows;
    wherein said second inlet conduit passageway, said second inlet port, and said mixing chamber define a second fluid flow path in which a second fluid flows; and
    wherein said second fluid mixes with said first fluid in said mixing chamber to decrease said outlet conduit passageway pressure differential.

3. The method of claim 2, further comprising disposing a first valve within said first fluid flow path to regulate flow of said first fluid.

4. The method of claim 3, wherein said first valve comprises a unidirectional first valve configured to:
    allow a first directional flow of said first fluid from said connector first open end toward said connector second open end; and
    interrupt a second directional flow of said first fluid from said connector second open end toward said connector first open end.

5. The method of claim 4, further comprising disposing a second valve within said second fluid flow path to regulate flow of said second fluid.

6. The method of claim 5, wherein said second valve comprises a unidirectional second valve configured to:
    allow a first directional flow of said second fluid from said connector second open end toward said mixing chamber; and interrupt a second directional flow of said second fluid from said mixing chamber toward said connector second open end.

7. The method of claim 1, further comprising:
providing discrete first and second housings;
wherein said first housing defines said connector first open end; and
wherein said second housing defines said connector second open end.

8. The method of claim 7, wherein said first and second housings releasably matably engage with one another to provide said first fluid flow path between said connector first and second open ends.

9. The method of claim 8, further comprising coupling a latch assembly to said first and second housings;
wherein said latch assembly facilitates releasable matable engagement of said first and second housings.

10. The method of claim 1, further comprising:
operatively coupling a sensor module to a connector passageway which communicates between said connector first and second open ends, said connector passageway defined by a connector internal surface;
said sensor module configured to sense a parameter of a first fluid flowing in a first fluid flow path through said connector passageway.

11. The method of claim 10, wherein said sensor module comprises:
a sensor which generate a sensor signal; and
a microcontroller configured to receive, process, and transform said sensor signal.

12. The method of claim 11, wherein said sensor comprises at least one selected from the group consisting of: a fluid flow rate sensor, a fluid temperature sensor which senses a fluid temperature of said first fluid, a pH sensor which senses a fluid pH of said first fluid, a fluid conductivity sensor which senses a fluid conductivity of said first fluid, a fluid turbidity sensor which senses a fluid turbidity of said first fluid, a blood content sensor which senses an amount of blood in said first fluid, a protein content sensor which senses an amount of protein in said first fluid, and a dissolved gas sensor which senses an amount of dissolved gas in said first fluid.

13. The method of claim 11, wherein said sensor module comprises a transmitter configured to transmit a transmitter signal to a remote device.

14. A method of making a connector which couples to an outlet conduit to decrease an outlet conduit passageway pressure differential between outlet conduit opposing first and second ends, said connector comprising:
providing a mixing chamber;
fluidically coupling a first inlet port with a connector first open end and said mixing chamber;
fluidically coupling an outlet port with said mixing chamber and a connector second open end; and
fluidically coupling a second inlet port with said connector second open end and said mixing chamber;
wherein said connector second open end is configured to couple to an outlet conduit and a second inlet conduit; and
wherein said outlet conduit and said second inlet conduit are combined into a one-piece tubular construct.

15. The method of claim 14, wherein said connector second open end is configured to couple to said outlet conduit to fluidicly couple an outlet conduit passageway to said outlet port; and
wherein said connector second open end is configured to couple to said second inlet conduit to fluidicly couple a second inlet conduit passageway to said second inlet port.

16. The method of claim 14, wherein said outlet conduit passageway and said second inlet conduit passageway dispose in laterally adjacent relation to one another between one-piece tubular conduit opposing first and second ends.

* * * * *